US00RE49023E

(19) United States
(12) Reissued Patent
Isogai et al.

(10) Patent Number: US RE49,023 E
(45) Date of Reissued Patent: Apr. 12, 2022

(54) FUNDUS OBSERVATION APPARATUS

(71) Applicant: NIDEK CO., LTD., Gamagori (JP)

(72) Inventors: Naoki Isogai, Nishio (JP); Toshio Murata, Milpitas, CA (US)

(73) Assignee: NIDEK CO., LTD., Gamagori (JP)

(21) Appl. No.: 14/681,680

(22) Filed: Apr. 8, 2015

Related U.S. Patent Documents

Reissue of:
(64) Patent No.: 8,419,186
Issued: Apr. 16, 2013
Appl. No.: 12/894,551
Filed: Sep. 30, 2010

(30) Foreign Application Priority Data

Sep. 30, 2009 (JP) ..... 2009-228768

(51) Int. Cl.
*A61B 3/14* (2006.01)
*A61B 3/10* (2006.01)

(52) U.S. Cl.
CPC ..... *A61B 3/102* (2013.01)

(58) Field of Classification Search
CPC .. A61B 3/102; A61B 3/12; A61B 3/14; A61B 3/1225; A61B 5/004
USPC ..... 351/206, 221, 246, 205, 210, 208
See application file for complete search history.

(56) References Cited

U.S. PATENT DOCUMENTS 5,873,831 A 2/1999 Bernstein et al.
7,474,775 B2 * 1/2009 Abramoff ..... G06K 9/6277 351/206
7,488,071 B2 * 2/2009 Ogawa ..... A61B 3/14 351/206
7,506,978 B2 3/2009 Nanjo
7,510,282 B2 3/2009 Ueno et al.
7,824,035 B2 * 11/2010 Yamada et al. ..... 351/206
8,025,403 B2 * 9/2011 Maloca ..... A61B 3/102 351/205
9,655,517 B2 * 5/2017 Su ..... A61B 3/145
2004/0167742 A1 8/2004 Haisch
(Continued)

FOREIGN PATENT DOCUMENTS

JP 2008-029467 A 2/2008
JP A-2008-29467 2/2008

OTHER PUBLICATIONS

Apr. 10, 2018 Office Action issued in U.S. Appl. No. 15/262,708.
(Continued)

*Primary Examiner* — Woo H. Choi
(74) *Attorney, Agent, or Firm* — Oliff PLC

(57) ABSTRACT

A fundus observation apparatus that is capable of assisting an examiner in judging the presence or absence of abnormality in an examinee's eye based on a fundus tomographic image. The fundus observation apparatus includes an optical coherence tomography device that has an optical scanner for setting an image pickup position on a fundus of an examinee's eye, and is arranged to obtain a tomographic image of the fundus, and an information display unit that is arranged to display on a monitor the tomographic image obtained by the optical coherence tomography device and assisting information for assisting an examiner in performing judgment on the tomographic image, and the information display unit is arranged to change the assisting information based on image pickup information on the tomographic image.

15 Claims, 5 Drawing Sheets

(56) References Cited

U.S. PATENT DOCUMENTS

| | | | | |
|---|---|---|---|---|
| 2006/0025670 | A1 | 2/2006 | Kim et al. | |
| 2006/0187462 | A1* | 8/2006 | Srinivasan | A61B 3/102 356/479 |
| 2007/0091265 | A1 | 4/2007 | Kardon et al. | |
| 2007/0183760 | A1* | 8/2007 | Mizuno | A61B 3/12 396/18 |
| 2007/0222946 | A1* | 9/2007 | Fukuma | A61B 3/102 351/206 |
| 2007/0291277 | A1* | 12/2007 | Everett | A61B 3/102 356/497 |
| 2008/0273172 | A1 | 11/2008 | Spaide | |
| 2009/0033870 | A1 | 2/2009 | Hangai et al. | |
| 2009/0073387 | A1* | 3/2009 | Meyer | A61B 3/12 351/246 |
| 2009/0115964 | A1 | 5/2009 | Ueno | |
| 2009/0161826 | A1 | 6/2009 | Gertner et al. | |
| 2009/0190092 | A1* | 7/2009 | Tsukada | A61B 3/102 351/208 |
| 2010/0208204 | A1* | 8/2010 | Imamura | A61B 3/14 351/206 |
| 2010/0238403 | A1* | 9/2010 | Kobayashi | A61B 3/0058 351/206 |

OTHER PUBLICATIONS

Mar. 11, 2019 Office Action issued in U.S. Appl. No. 15/262,708.
Aug. 15, 2019 Office Action issued in U.S. Appl. No. 15/262,708.
Apr. 28, 2020 Office Action issued in U.S. Appl. No. 15/262,708.
Jun. 23, 2021 Office Action issued in U.S. Appl. No. 15/262,708.
Jan. 18, 2022 Notice of Allowance issued in U.S. Appl. No. 15/262,708.

* cited by examiner

FUNDUS OBSERVATION APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This is a Reissue of U.S. Pat. No. 8,419,186, issued Apr. 16, 2013, which issued from U.S. application Ser. No. 12/894,551, filed Sep. 30, 2010, which claims the benefit of Japanese Patent Application No. 2009-228768, Sep. 30, 2009.*

*More than one reissue application has been filed for the reissue of U.S. Pat. No. 8,419,186. The reissue applications are application Ser. No. 14/681,680 (the present application), and application Ser. No. 15/262,708, which is a Reissue Divisional of the present application.*

BACKGROUND OF THE INVENTION

1. Field of the Invention

The present invention relates to a fundus observation apparatus that observes a tomographic image of a fundus of an examinee's eye.

2. Description of Related Art

Conventionally, a fundus observation apparatus that obtains a tomographic image of a fundus of an examinee's eye using an optical interference technique (i.e., an optical coherence tomography apparatus) is used for evaluating the condition of the examinee's eye (see Japanese Patent Application Laid-open Publication No. 2005-29467). This kind of fundus observation apparatus controls a monitor to display a fundus image picked up by using infrared light. An examiner selects a given region (portion) of the fundus image and obtains a fundus tomographic image of the selected region. The examiner observes the obtained fundus tomographic image and judges the presence or absence of abnormality in the examinee's eye.

However, a great deal of expertise is required for judging the presence or absence of abnormality in the examinee's eye based on the fundus tomographic image because the fundus tomographic configuration varies depending on the selected region of the fundus image.

SUMMARY OF THE INVENTION

An object of the invention is to overcome the problems described above and to provide a fundus observation apparatus that is capable of assisting an examiner in judging the presence or absence of abnormality in an examinee's eye based on a fundus tomographic image.

To achieve the objects and in accordance with the purpose of the present invention, a fundus observation apparatus has an optical coherence tomography device that has an optical scanner for setting an image pickup position on a fundus of an examinee's eye, and is arranged to obtain a tomographic image of the fundus, and an information display unit that is arranged to display on a monitor the tomographic image obtained by the optical coherence tomography device and assisting information for assisting an examiner in performing judgment on the tomographic image, and the information display unit is arranged to change the assisting information based on image pickup information on the tomographic image.

According to the present invention, the examiner is assisted in judging the present or absence of abnormality in the examinee's eye based on the fundus tomographic image.

Additional objects and advantages of the invention are set forth in the description which follows, are obvious from the description, or may be learned by practicing the invention. The objects and advantages of the invention may be realized and attained by the fundus observation apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention, In the drawings.

DETAILED DESCRIPTION OF THE PREFERRED EMBODIMENTS

Figure 1:
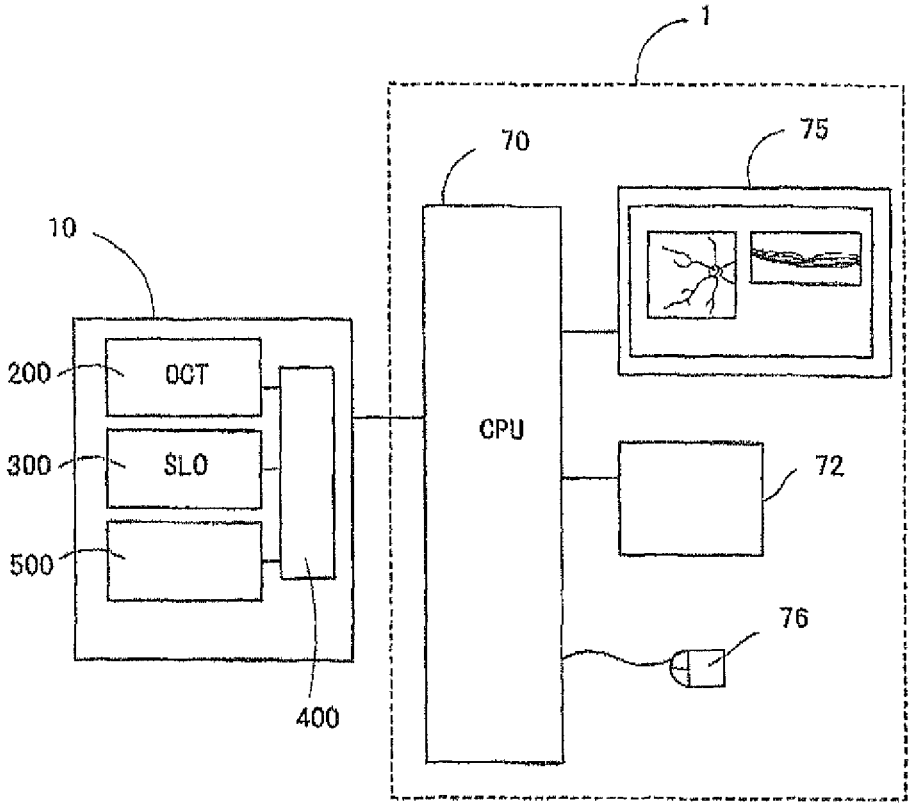
FIG. 1 is a block diagram for explaining the configuration of a fundus observation apparatus according to a preferred embodiment of the present invention.

A detailed description of one preferred embodiment of a fundus observation apparatus embodied by the present invention is provided below with reference to the accompanying drawings. FIG. 1 is a block diagram for explaining the configuration of the fundus observation apparatus according to the preferred embodiment of the present invention.

A fundus observation apparatus 1 is arranged to observe on a monitor a fundus image obtained by a fundus photographing apparatus 10. The fundus observation apparatus 1 includes a CPU (arithmetic control unit) 70, a mouse (operation input unit) 76, a memory (storage unit) 72, and a monitor 75. These units are connected electrically to the CPU 70 via buses or other mechanisms.

The CPU 70 controls operations of these units under an ophthalmic observation program and various control programs that are stored in the memory 72. By executing the ophthalmic observation program on the computer, the fundus observation apparatus 1 becomes operational. The CPU 70 controls the display screen on the monitor 75 following the ophthalmic observation program. The ophthalmic observation program according to the preferred embodiment of the present invention has the function of displaying photographed images and various measurement results on the monitor 75, and an analysis mode function of determining whether a photographed portion is normal or abnormal by analyzing a tomographic image.

It is also preferable that an arithmetic processing unit, an input unit, a storage unit, and a display unit that are included in a commercially available PC (personal computer) are used for the CPU 70, the mouse 76, the memory 72, and the monitor 75, and the ophthalmic observation program is installed on the commercially available PC.

The fundus photographing apparatus 10 arranged to photograph an image of a given portion of an examinee's eye is connected to the fundus observation apparatus 1. As shown in FIG. 1, the fundus photographing apparatus 10 includes an interference optical system (OCT optical system) 200 arranged to obtain a tomographic image of a fundus of the examinee's eye, a front observation optical system 300 arranged to obtain a front image of the fundus, a control unit 400, and a fixation target projection unit 500 capable of fixating the examinee's eye and changing the fixation direction. Thus, the fundus photographing apparatus 10 can photograph a fundus portion of the examinee's eye. For a detailed configuration of the fundus photographing apparatus 10, please to refer to Japanese Patent Application Laid-open Publication No. 2008-29467.

The fundus photographing apparatus 10 is arranged to select a given region of the fundus observation image (SLO image) obtained by picking up an image of the fundus, and obtain a fundus tomographic image of the selected region using fundus OCT.

The interference optical system 200 includes a first scanning unit (optical scanner) arranged to scan first measurement light emitted from a first light source on the fundus, and a first photodetector arranged to photo-receive interference light that is obtained by combining reference light resulting from light emitted from the first light source and reflection light of the first measurement light that is projected onto the fundus. Accordingly, the interference optical system 200 has the configuration of a so-called ophthalmic optical coherence tomography (OCT) device. For the configuration of the interference optical system 200, Spectral-domain OCT (SD-OCT) using a spectrometer, Swept-source OCT (SS-OCT) using a wavelength variable light source, or Time-domain OCT (TD-OCT) may be used.

The front observation optical system 300 includes a second scanning unit (optical scanner) arranged to scan second measurement light (e.g., infrared light) emitted from a second light source two-dimensionally on the fundus, and a second photodetector arranged to photo-receive the light reflected from the fundus through a confocal opening disposed at a position substantially conjugate with the fundus. Accordingly, the front observation optical system 300 has the configuration of a so-called ophthalmic scanning laser ophthalmoscope (SLO). For the configuration of the front observation optical system 300, a so-called fundus camera type configuration may be used.

The control unit 400 controls the members of the fundus photographing apparatus 10 to obtain the tomographic image (OCT image) based on a photo-receiving signal outputted from the first photodetector of the interference optical system 200 and obtain the front image (SLO image) based on a photo-receiving signal outputted from the second photodetector of the front observation optical system 300.

The fixation target projection unit 500 includes a visible light source that emits visible light, and is arranged to change the photographed portion by two-dimensionally changing the fixation position of the examinee's eye. The fixation target projection unit 500 may have various configurations such as a configuration that the fixation position is adjusted by using the lighting position of LEDs arranged in a matrix and a configuration that light emitted from a light source is scanned by an optical scanner and the fixation position is adjusted by controlling lighting of the light source.

The fundus observation apparatus 1 and the fundus photographing apparatus 10 are connected to each other on a LAN or other mechanisms, and signals are sent and received therebetween. Various data obtained in the fundus photographing apparatus 10 (e.g., tomographic image data, front image data, various photographing conditions for image obtainment (e.g., image pickup information, selected region information, test date and time)) are transferred to the memory 72 that is a database. The control unit 400 of the fundus photographing apparatus 10 controls the interference optical system 200, the front observation optical system 300, and the fixation target projection unit 500 based on operation signals outputted from the mouse 76.

Descriptions of the operations of the apparatuses having the configurations described above are provided. First, the tomographic image is obtained by using the fundus photographing apparatus 10. As a preliminary preparation to the image obtainment, patient information (e.g., ID number, name, age, sex, major complaint, comments) is inputted. On the monitor 75, the tomographic image obtained by the interference optical system 200, the front image obtained by the front observation optical system 300, and a setting screen for setting the various photographing conditions are displayed.

When an image pickup portion is selected, the control unit 400 controls the fixation target projection unit 500 to move the fixation position to a position corresponding to the selected image pickup portion. For example, when a macula portion photographing mode is selected, the fixation position is set at the center, and when a papilla portion photographing mode is selected, the fixation position is set toward the nose on a slightly upper side. It should be noted that the fixation positions of right and left eyes are substantially symmetrical along the horizontal direction. In the preferred embodiment of the present invention, a targeted image pickup portion and the fixation position provided by the fixation target photographing unit are associated with each other, based on which the fixation position is set. Accordingly, a tomographic image of a fundus portion the examiner desires is easily obtained.

Figure 2:
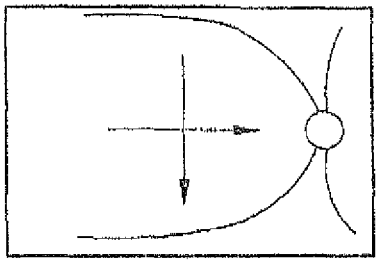
FIG. 2 is a view showing a case where a cross-line scan in horizontal and vertical directions is selected in a macula portion photographing mode.
Figure 3:
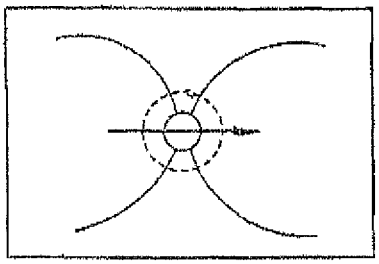
FIG. 3 is a view showing a case where a horizontal line scan or a circle scan is selected in a papilla portion photographing mode.

Then, a scanning pattern of the measurement light (e.g., line, cross-line, raster, circle, radial) is selected. For example, in the macula portion photographing mode, a cross-line scan in the horizontal and vertical directions is selected (see FIG. 2), and in the papilla portion photographing mode, a horizontal line scan or a circle scan is selected (see FIG. 3). Alternatively, multi line photographing shown in FIG. 4 may be performed.

Then, alignment and focusing with respect to the fundus are performed using the front image obtained by the front observation optical system 300. When a trigger of photographing is outputted, the control unit 400 drives the first scanning unit based on the previously set photographing conditions to obtain a tomographic image corresponding to the selected scanning pattern. The obtained tomographic image and the corresponding front image (SLO image), image pickup information (e.g., fixation position information, image pickup portion information, right and left eye information), and selected region information (e.g., scanning pattern, scanning position, scanning range) are stored in the memory 72. The image pickup information described above may be information when the front image corresponding to the tomographic image is obtained.

Then, the tomographic image and the front image that are obtained as described above are observed by using the fundus observation apparatus 1. When an analysis mode is selected, the CPU 70 detects information on retinal layers in the tomographic image stored in the memory 72 through image processing. Then, the CPU 70 analyses the detection result of the retinal layers by a given determination criterion, and determines whether the photographed portion is normal or abnormal. Then, the CPU 70 controls the monitor 75 to display the tomographic image and the determination result.

The determination result may be used as assisting information for assisting the examiner in judging the fundus tomographic image. In such a case, the CPU 70 changes the determination criterion based on at least one of the image pickup information and the selected region information on the fundus tomographic image, and controls the monitor 75 to display the determination result obtained by the changed determination criterion as the assisting information. In other words, the CPU 70 changes information that is to be displayed as the assisting information based on at least one of the image pickup information and the selected region information on the fundus tomographic image.

The detection of the retinal layers is performed such that the CPU 70 analyzes a brightness level of the tomographic image and detects a region corresponding to a given retinal layer (e.g., retinal surface, retinal pigment epithelium layer). In addition, the determination of the photographed portion may include thickness determination of the retinal layers, shape determination, and size determination of the given portion. In addition, a database that stores thicknesses of retinal layers, shapes of given portions, sizes of the give portions of a normal eye may be used as the standard for the image determination criterion.

FIGS. 5A to 5D are views showing specific examples of a determination criterion for analyzing an image obtained in the macula portion photographing mode. In an image of a macula portion, a characteristic image of the retinal surface having a recessed portion at the center is generally obtained. The CPU 70 selects the determination criterion for determining the macula portion based on photographing mode information, and determines the detection result on the retinal layers by the determination criterion.

In the determination of the macula portion image, the CPU 70 determines that the photographed portion is normal if the thickness between the retinal layers is within a given range and the retinal layer shape is normal (see FIG. 5A), and controls the monitor 75 to display the determination result. It should be noted that if the photographed portion is normal, the display is not necessarily performed.

On the other hand, the CPU 70 determines that the photographed portion is abnormal if the retinal layer shape is unusual (for example, the recessed portion is not detected (see FIG. 5B), the retinal layer has an irregular shape (see FIG. 5C)), if the thickness between the retinal layers is out of the given range (see FIG. 5D), or if the retinal layers are not detected, and controls the monitor 75 to display the determination result. For example, a message "the macula portion is abnormal" is displayed. In addition, the CPU 70 may highlight a portion corresponding to the abnormal portion (for example, an image region corresponding to the macula portion is circled). The reason of the determination that the photographed portion is abnormal, for example, the recessed portion cannot be detected, may be displayed.

The CPU 70 may change the determination criterion according to the scanning direction of the measurement light on the fundus, and determine whether the photographed portion is normal or abnormal by the determination criterion. This operation may be used when tomographic images of the same portion (e.g., the macula portion) are obtained in different scanning directions.

Figure 6A:
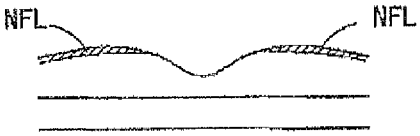
FIGS. 6A and 6B are views showing specific examples of a determination criterion for performing thickness determination on a retinal optic nerve fiber layer (NFL)

For example, this operation may be used when the layer thickness determination is performed on a retinal optic nerve fiber layer (NFL). In the case of determining a vertical line scan image obtained by scanning the measurement light in the vertical (up and down) direction (see FIG. 6A), the CPU 70 determines that the photographed portion is abnormal if, on the image, at least one of thicknesses of the nerve fiber layer that is symmetrically formed on the right side and the left side with respect to the macula portion are out of a given range (also if at least one of the thicknesses are not detected). The CPU 70 determines that the photographed portion is normal if both of the thicknesses of the nerve fiber layer that is symmetrically formed on the right side and the left side with respect to the macula portion are in the given range.

Figure 6B:
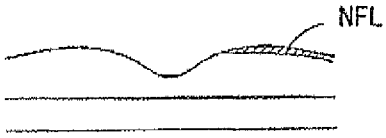

In the case of determining a horizontal line scan image obtained by scanning the measurement light in the horizontal direction (FIG. 6B), the CPU 70 determines that the photographed portion is abnormal if, on the image, the thickness of the nerve fiber layer on the papilla portion side with respect to the macula portion (the right side in a right eye and the left side in a left eye) is out of the given range (also if the thickness is not detected). The CPU 70 determines that the photographed portion is normal if the thickness is within the given range. It should be noted that the CPU 70 does not determine that the photographed portion is abnormal even if the thickness of the nerve fiber layer on the opposite side to the papilla portion with respect to the macula portion is out of the given range (also if the thickness is not detected). In the thickness determination of the nerve fiber layer, the use of the horizontal line scan image may be avoided.

The change of the determination criterion according to the scanning direction and the display of the determination results that the photographed portion is normal or abnormal favorably assist an unaccustomed examiner in performing image diagnosis. The pattern of the nerve fiber layer extending in the retina is symmetric with respect to the macula portion in the vertical direction and is asymmetric with respect to the macula portion in the horizontal direction. Thus, an unaccustomed examiner could judge that the photographed portion is abnormal in a horizontal line scan image in which an image region corresponding to the nerve fiber layer is not visually observed in both of right and left regions. However, the technique described above can prevent the examiner from making such a judgment error.

The present invention is not limited to the scanning patterns described above. It is also preferable that tomographic images that are obtained at given angles (e.g., 30 degrees, 45 degrees) having a given photographed portion at the center are analyzed by different determination criteria. In this case, because the extending pattern of the nerve fiber layer differs according to the scanning direction, the image diagnosis is performed in consideration of this point.

In addition to the determination results, the CPU 70 may control the monitor 75 to display assisting information for assisting the examiner in performing the image diagnosis. In addition, the CPU 70 may control the monitor 75 to display different assisting information according to the scan direction of the measurement light.

For example, in the case of displaying the vertical line scan image (see FIG. 6A), the CPU 70 controls the monitor 75 to display a message "if the eye is normal, the nerve fiber layer is symmetric with respect to the macula portion", or to perform highlight display in the image display. In the case of displaying the horizontal line scan image (see FIG. 6B), the CPU 70 controls the monitor 75 to display a message "even if the eye is normal, the optical fiber layer is asymmetric with respect to the macula portion", or to perform highlight display in the image display.

Figure 7A:
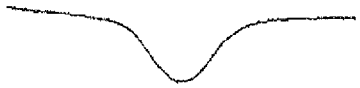
FIGS. 7A and 7B are views showing specific examples of a determination criterion for analyzing an image obtained in the papilla portion photographing mode.
Figure 7B:
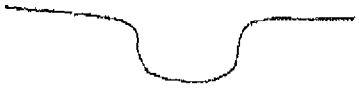

FIGS. 7A and 7B are views showing specific examples of a determination criterion for analyzing an image obtained in the papilla portion photographing mode. In an image of a papilla portion, a characteristic image of the papilla portion having a recessed portion at the center that is larger than the macula portion is obtained by the line scan. The CPU 70 selects the determination criterion for determining the papilla portion based on the photographing mode information and the scanning pattern information, and determines the detection result on the retinal layers by the determination criterion. In other words, the CPU 70 changes the determination criterion according to the scanning pattern.

In the determination of a papilla portion image obtained by the line scan, the CPU 70 determines that the photographed portion is normal if the size of the recessed portion (or a C/D ratio of the recessed portion) is within a given range (see FIG. 7A), and controls the monitor 75 to display the determination result. The CPU 70 determines that the photographed portion is abnormal if the size of the recessed portion is out of the given range (see FIG. 7B), and controls the monitor 75 to display the determination result. For example, a message "the papilla portion is abnormal" is displayed. The CPU 70 may determine whether the thickness between or the shape of the retinal layers is normal or abnormal as in the case of the macula portion.

Figure 8A:
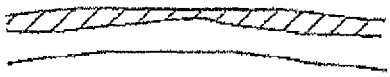
FIGS. 8A and 8B are views showing specific examples of a determination criterion for determining a papilla portion image obtained by the circle scan.
Figure 8B:
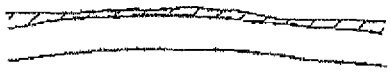

In the determination of a papilla portion image obtained by the circle scan, the CPU 70 determines that the photographed portion is normal if the thickness of the nerve fiber layer is within a given range (see FIG. 8A), and controls the monitor 75 to display the determination result. The CPU 70 determines that the photographed portion is abnormal if the thickness of the nerve fiber layer is out of the given range (see FIG. 8B), and controls the monitor 75 to display the determination result.

As described above, whether the photographed portion is normal or abnormal can be properly determined by changing the determination criterion according to the image pickup portion information. Thus, an examiner who lacks special knowledge about the image diagnosis based on the tomographic image can easily judge whether the photographed portion is normal or abnormal based on the tomographic image.

By performing the line scan or the raster scan at a plurality of different positions on the fundus and obtaining a plurality of tomographic images by the fundus photographing apparatus 10, a wide range tomographic image is obtained. The CPU 70 may specify an image (or a plurality of images) including a characteristic portion from among the obtained plurality of images, and perform the image determination described above.

Figure 4:
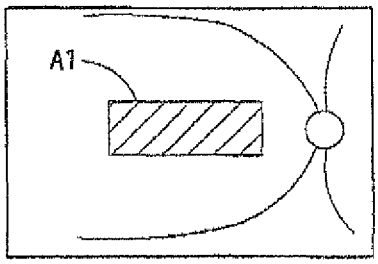
FIG. 4 is a view showing a case where multi line photographing is performed.
Figure 5A:
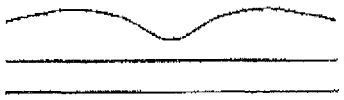
FIGS. 5A to 5D are views showing specific examples of a determination criterion for analyzing an image obtained in the macula portion photographing mode.
Figure 5B:
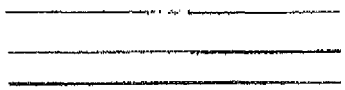
Figure 5C:
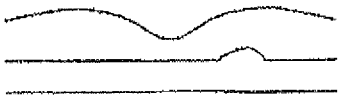
Figure 5D:
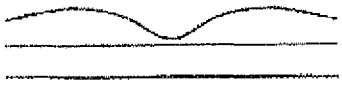

For example, the control unit 400 controls the driving of the first scanning unit to perform the multi line scan (or the raster scan) within a given region A1 as shown in FIG. 4. Thus, a plurality of tomographic images including the macula portion are obtained. The obtained plurality of tomographic images are stored in the memory 72 and are observed by the fundus observation apparatus 1.

The CPU 70 detects the sizes of the recessed portions in the tomographic images, selects one (or more) of the tomographic images in which the recessed portion is largest as an image for the analysis based on the detection result, and shifts to the analysis described above. Then, the CPU 70 determines whether the photographed portion is normal or abnormal. With this technique, the position of the photographed portion is accurately specified even if the position of a targeted image pickup portion is different among individuals, which allows the examiner to perform the image diagnosis adequately.

The present invention is not limited to the technique described above. The CPU 70 may analyze each of the plurality of tomographic images, perform the determination of the presence or absence of the abnormal portion and the specification of the position of the abnormal portion through image processing, and control the monitor 75 to display the results.

Figure 9:
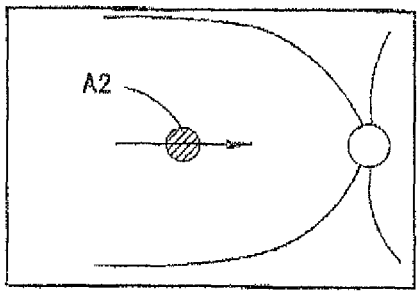
FIG. 9 is a view showing a specific example of a determination criterion for analyzing a front image.

In the configuration described above, the CPU 70 may determine the abnormal portion by analyzing the front image obtained by the front observation optical system 300. FIG. 9 is a view showing a specific example of a determination criterion for analyzing the front image. In the front image, the abnormal portion appears as a brightness change (bright and dark) that does not appear in a normal eye (see a region A2 in FIG. 9).

The CPU 70 selects a determination criterion for determining the front image and performs determination of the presence or absence of the brightness change by the determination criterion. For example, in the determination of the front image, the CPU 70 detects a portion having a brightness level lower than a given level or a portion having a brightness level higher than the given level through image processing, and performs the determination of the presence or absence of the abnormal portion and the specification of the position of the abnormal portion.

Adjustment of Image Pickup Position Based on Tomographic Image Analysis

The fundus photographing apparatus 1 may obtain a tomographic image of a desired portion by performing the analysis described above. For example, the control unit 400 may analyze the tomographic image obtained by the interference optical system 200, specify a targeted image pickup portion through image processing, and adjust the image pickup position so as to obtain an image of the targeted image pickup portion.

In this case, the control unit 400 successively obtains and analyses the tomographic images while adjusting the scanning position of the first scanning unit (an oscillation angle, the center position of the oscillation angle) in order that the scanning position of the measurement light on the fundus may correspond to the position at which a characteristic image (e.g., an image having a characteristic shape as the image pickup portion) is obtained.

For example, the control unit 400 controls the driving of the first scanning unit to perform the multi line scan or the raster scan. Then, the control unit 400 adjusts the image pickup position so as to obtain the tomographic image having the recessed portion corresponding to the macula portion at the center. In this case, the control unit 400 detects the sizes of the recessed portions in the successively obtained tomographic images. If the control unit 400 determines that the tomographic image having the recessed portion corresponding to the macula portion is obtained based on the detection result, the control unit 400 fixes the scanning position of the measurement light. Then, the control unit 400 successively obtains the tomographic images at the scanning position and outputs the images as a moving image.

In the configuration described above, the control unit 400 performs the determination whether the photographed portion is normal or abnormal and the specification of the position of the abnormal portion through image processing while successively obtaining and analyzing the tomographic images. The control unit 400 may control the driving of the first scanning unit to obtain the tomographic image of the abnormal portion.

Figure 10A:
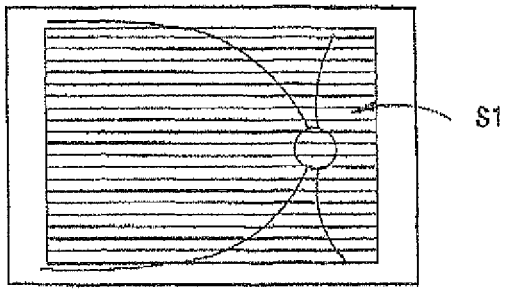
FIGS. 10A to 10C are views for explaining adjustment of an image pickup position based on wide range tomographic image analysis.
Figure 10B:
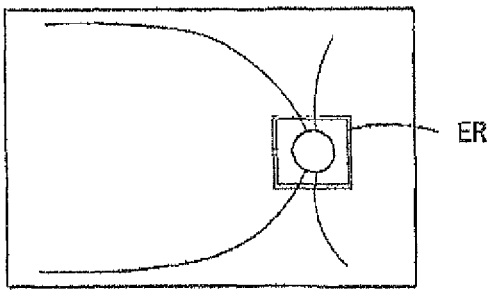
Figure 10C:
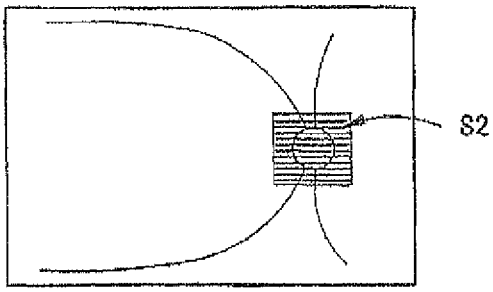

Screening Using Wide Range Tomographic Image and Obtainment of Tomographic Image of Abnormal Portion FIGS. 10A to 10C are views for explaining adjustment of the image pickup position based on wide range tomographic image analysis. For example, the control unit 400 controls the driving of the first scanning unit to scan the measurement light two-dimensionally in a wide range of the fundus and obtain a wide range tomographic image of the fundus (a first tomographic image) (see a hatched portion S1 in FIG. 10A, for example). In this case, it is preferable that the scanning range is set such that the macula portion and the papilla portion are included in the photographing range (e.g., a rectangular region 9 mm long and 9 mm wide, a rectangular region 12 mm long and 12 mm wide). For the scanning pattern, the multi line scan or the raster scan is used, for example. Thus, a plurality of tomographic images that provide fundus tomographic information in the wide range can be obtained.

Next, the control unit 400 specifies the abnormal portion by analyzing the obtained first tomographic image through image processing (first analysis). The control unit 400 may perform analysis appropriate to each of the retinal portions in the tomographic image or may analyze the whole first tomographic image by one criterion (details are provided later).

The control unit 400 outputs the obtained first tomographic image and the front image that is obtained substantially concurrently with the first tomographic image on the monitor 75, and outputs a result of the first analysis on the monitor 75. The control unit 400 may successively drive the interference optical system 200 and the front observation optical system 300 and control the monitor 75 to display a graphic showing the analysis result (for example, display a mark at a portion corresponding to the abnormal portion) in the state of being superimposed on the tomographic observation images and the front observation image that are obtained in real time as moving images (see a mark ER in FIG. 10B). Thus, the examiner is allowed to check the abnormal portion based on the observation images during examination.

Next, the control unit 400 sets a region that is specified to be the abnormal portion as a scanning range of the measurement light and controls the driving of the first scanning unit to obtain a second tomographic image (see a hatched portion S2 in FIG. 10C). The control unit 400 may set the scanning range by obtaining the scanning position corresponding to the region that is specified to be the abnormal portion (the driving position of the first scanning unit) based on the relation between the first tomographic image and the scanning position.

In the case of obtaining the second tomographic image, it is preferable to use the scanning pattern that is suitable for the image obtainment of the abnormal portion. In addition, it is preferable that the scanning range of the second tomographic image is narrower than the scanning range of the first tomographic image (the wide range tomographic image) of the fundus and includes the whole abnormal portion. For example, the raster scan is performed on a rectangular region that is adjusted to the size of the abnormal portion. In addition, the fixation position is preferably set at a position that is suitable for the image obtainment of the abnormal portion. It is also preferable that a plurality of tomographic images are obtained at the same abnormal portion and an averaged image thereof is obtained.

In the case of obtaining the second tomographic image, the control unit 400 may automatically shift to the obtainment of the second tomographic image based on the analysis result of the first tomographic image, or may start the obtainment of the second tomographic image using an operation signal from the mouse 76 as a trigger.

If a plurality of abnormal portions are detected, the control unit 400 obtains the second tomographic image in a scanning range that is narrower than the scanning range of the wide range tomographic image and includes the plurality of abnormal portions. In addition, the control unit 400 may set scanning ranges for the abnormal portions and obtain tomographic images of the abnormal portions successively.

Analysis Appropriate to Each of Retinal Portions

In the case of performing analysis appropriate to each of the retinal portions, the control unit 400 specifies regions corresponding to the macula portion and the papilla portion in the obtained tomographic images through image processing. Then, the control unit 400 performs analysis appropriate to each of the specified regions. When the macula portion is specified, the control unit 400 analyses the macula portion in the tomographic images by using the analysis technique used in the macula portion photographing mode described above. If the papilla portion is specified, the control unit 400 analyses the papilla portion in the tomographic images by using the analysis technique used in the papilla portion photographing mode described above.

In the case of specifying the given portion in the tomographic image, the macula portion and the papilla portion can be extracted based on positions, brightness values, and shapes in the tomographic image. For the macula portion that has brightness lower than that of its peripheral portion and has a circular shape, image processing is performed so as to extract an image region that shows these properties. For the papilla portion that has brightness higher than that of its peripheral portion and has a circular shape, image processing is performed so as to extract an image region that shows these properties. It is also preferable that the positions of the macula portion and the papilla portion are specified by using the front image, and the results are used for the analysis of the tomographic image.

For example, if the CPU 70 determines that the papilla portion is abnormal, the control unit 400 sets the papilla portion as the scanning range of the measurement light and controls the driving of the first scanning unit to obtain the tomographic image of the papilla portion. The scanning range is set to be narrower than the scanning range of the wide range tomographic image described above and to include the whole papilla (for example, 4.5 mm long and 4.5 mm wide). For the papilla portion, the circle scan or the radial scan may be performed.

Analysis on Whole Fundus

In the case of analyzing the whole tomographic images by one criterion, the control unit 400 calculates the thicknesses of the retinal layers (e.g., retinal surface layer, retinal pigment epithelium layer) in the tomographic images. The control unit 400 two-dimensionally obtains a position at which the thickness is out of the given range. A result of comparison between the layer thicknesses of the examinee's eye and layer thicknesses of a normal eye with respect to the horizontal and vertical directions may be used. In addition, the sum of the layer thicknesses may be used in the layer thickness analysis.

The control unit 400 sets the abnormal portion as the scanning range of the measurement light, and controls the driving of the first scanning unit to obtain the tomographic image of the abnormal portion. The scanning pattern that is suitable for the image obtainment of the abnormal portion is preferably used.

With the configuration described above, the two-dimensional tomographic image obtained in the wide scanning range is analyzed, and the abnormal portion in the whole fundus is specified, so that the tomographic image can be obtained with the photographing conditions suitable for the abnormal portion. Because the scanning range is narrower than the wide scanning range and includes the whole fundus, deviation between the images is minimized, and the tomographic image of the abnormal portion can be obtained with high resolution.

The control unit 400 analyzes the second tomographic image (second analysis) and outputs the analysis result on the monitor 75. Thus, a precise analysis result of the abnormal portion is obtained. In this case, the specification and the analysis of the abnormal portion on the fundus can be smoothly performed by specifying the abnormal portion through screening on the whole fundus and precisely analyzing the abnormal portion.

The control unit 400 outputs the second tomographic image and the front image that is obtained substantially concurrently with the second tomographic image on the monitor 75, and outputs the result of the second analysis on the monitor 75. In addition, the control unit 400 outputs the first tomographic image and the second tomographic image on the monitor 75. At least one of the first tomographic image and the second tomographic image may be displayed in the form of a three-dimensional tomographic image.

Correction of Positional Deviation Between First Tomographic Image and Second Tomographic Image In the configuration described above, the control unit 400 may correct the image pickup position of the tomographic image by obtaining the fundus front image that is obtained concurrently with the first tomographic image and calculating a positional deviation between the above fundus front image and the fundus front image that is obtained concurrently with the second tomographic image. The front image may be an image that is obtained by using data forming a two-dimensionally obtained tomographic image (e.g., an integrated image of tomographic images in the depth direction, an integrated value of spectral data at positions in the horizontal and vertical directions).

In addition, the control unit 400 may perform matching between the tomographic image corresponding to the abnormal portion in the first tomographic image and the tomographic images that are continually obtained when obtaining the second tomographic image through image processing, and correct the scanning position so as to obtain the tomographic image at a substantially matching position (the front image may be used instead of the tomographic image). For example, the image of the abnormal portion in the first tomographic image is set as a template image, and template matching is performed between the tomographic images continually obtained and the template image. The scanning position is adjusted so that a correlation may become highest.

Screening Using Wide Range Tomographic Image and Obtainment of Tomographic Image of Characteristic Portion The above descriptions have been given on the case where the tomographic image of the abnormal portion is obtained. However, it is essential only that a tomographic image of a given portion in a wide range tomographic image be obtained by a screening scan.

For example, the control unit 400 may specify a characteristic portion (e.g., papilla portion, macula portion) by analyzing the obtained first tomographic image through image processing, and adjust the image pickup position so as to obtain a tomographic image of the specified characteristic portion. As for the technique of specifying the given portion in the tomographic image, please refer to "ANALYSIS APPROPRIATE TO EACH OF RETINAL PORTIONS" provided above.

Selective Storing of Tomographic Images

The control unit 400 may control the driving of the first scanning unit to perform the multi line scan or the raster scan, and store only the tomographic images that do not meet the given image determination criterion and are determined to be abnormal in the memory 72.

Adjustment of Image Pickup Position Based on Front Image Analysis

The control unit 400 may analyze the front image obtained by the front observation optical system 300, perform the determination of the presence or absence of the abnormal portion and the specification of the position of the abnormal portion, and adjust the image pickup position by the interference optical system 200 so as to obtain the tomographic image of the abnormal portion. The technique of the determination is the same as that of the front image analysis, and descriptions thereof are omitted. Accuracy in specifying the abnormal portion is improved by specifying the abnormal portion based on both of the analysis result on the tomographic image and the analysis result on the front image, and adjusting the image pickup position.

When the abnormal portion is specified, the control unit 400 obtains the tomographic image by controlling the driving of the first scanning unit in order that the scanning position of the measurement light on the fundus may correspond to the abnormal portion (e.g., the portion A2 in FIG. 9).

When the scan is performed on the abnormal portion, the control unit 400 may control the fixation target projection unit 500 with the driving position of the optical scanner being fixed, and guide a line of sight of the examinee's eye by moving the fixation position.

When the image obtainment, the analysis, and the determination are finished, the obtained images, the analysis results, and the photographing conditions (the image pickup information, the selected range information) are stored in association with the patient information. This information can be used as information for performing alignment with respect to the same portion at the time of re-photographing. In other words, the CPU 70 controls the memory 72 to store the photographing conditions including the fixation position (photographed portion) and the image pickup position (scanning position) in association with the photographed images, and reconstitute the photographing conditions at the time of re-photographing.

The alignment may be performed using the shape in the stored retinal layer detection result as a characteristic. In this case, the control unit 400 detects the shape in the tomographic image stored in the memory 72 and successively analyzes tomographic images obtained by the interference optical system 200. The control unit 400 may control the driving of the first scanning unit based on the analysis result and the detection result, and adjust the image pickup position so as to obtain tomographic images of the same portion that has the shape in the detection result.

In the above configuration, the analysis is performed using the two-dimensional tomographic image. However, the present invention is not limited thereto. The analysis may be performed using a three-dimensional image. In this case, determination whether a three-dimensional shape include a characteristic shape or not is performed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus observation apparatus comprising:

an optical coherence tomography device that has an optical scanner [for setting an] *configured to set* image pickup [position] *positions* on a fundus of an examinee's [eye, and is arranged] *eye and* to obtain a tomographic image of the fundus *according to any one of a plurality of photographing modes, each mode corresponding to a distinct image pickup position of the image pickup positions*;

[an information display unit that is arranged to display on a monitor] *a display that displays* the tomographic image obtained by the optical coherence tomography device and assisting information for assisting an examiner in performing judgment on the tomographic image; [and]

*a front fundus image pickup device configured to obtain a front image of the fundus;*

*a first non-transitory computer readable medium storing a first program for use with a processor, the first program causing the processor to execute steps comprising:*

*receiving an instruction signal by the examiner to select one photographing mode among the plurality of photographing modes,*

[an arithmetic analysis unit that is arranged to detect] *detecting* information on layers of the fundus in the tomographic image through image processing, [and determines the tomographic image by determining] *analyzing* the detected layer information [by a given determination criterion,] *in the tomographic image and performing a judgment as to whether the tomographic image satisfies a determination criterion,*

*changing the determination criterion depending on the selected photographing mode,*

*changing the assisting information based on the selected photographing mode and the display displays a first determination result as the assisting information,*

*detecting brightness information on the front image obtained by the front fundus image pickup device through the image processing, and*

*determining the front image by determining the detected brightness information by the determination criterion; and*

*a second non-transitory computer readable medium storing a second program for use with a controller, the second program causing the controller to execute a steps comprising:*

*controlling driving of the optical scanner to change the image pickup position on the fundus based on the photographing mode that is selected by the instruction signal,*

[wherein the information display unit is arranged to change the assisting information based on image pickup information on the tomographic image;

the arithmetic analysis unit is arranged to change the determination criterion based on at least the image pickup information; and the information display unit is arranged to display a first determination result obtained by the arithmetic analysis unit as the assisting information on the monitor]

*controlling a fixation position depending on the photographing mode in controlling the driving of the optical coherence tomography device depending on the photographing mode, and*

*emitting visible light toward the examinee's eye and guiding a line of sight of the examinee's eye by adjusting the position at which the visible light is projected on the fundus such that, when the optical coherence tomography device is in macula portion photographing mode, the fixation position is moved to a position corresponding to a position of the macula, and, when the optical coherence tomography device is in papilla portion photographing mode, the fixation position is moved to a position corresponding to a position of the papilla.*

2. The fundus observation apparatus according to claim 1, wherein [the arithmetic analysis unit uses] *performing the judgment as to whether the tomographic image satisfies the determination criterion includes using* a normal eye database as the determination criterion.

3. The fundus observation apparatus according to claim 1, [further comprising: a control unit that is arranged to control driving of the optical scanner to change the image pickup position on the fundus,] wherein [the arithmetic analysis unit is arranged to specify] *the first program further causes the processor to execute specifying* an abnormal portion in the tomographic image based on the first determination result or [specify] *specifying* a characteristic portion in the tomographic image through the image processing, and the [control unit is arranged to adjust] *second program further causes the controller to execute adjusting* the image pickup position so as to obtain the tomographic image including one of the abnormal portion and the characteristic portion [that are specified by the arithmetic analysis unit].

4. The fundus observation apparatus according to claim 3, wherein the [control unit is arranged to obtain] *second program further causes the controller to execute obtaining* a first tomographic image of a wide range of the fundus by two-dimensionally scanning measurement light on the fundus using the optical scanner,

[the arithmetic analysis unit is arranged to specify] *the first program further causes the processor to execute specifying* one of the abnormal portion and the characteristic portion in the first tomographic image, and the [control unit is arranged to obtain] *second program further causes the controller to execute obtaining* a second tomographic image by scanning the measurement light in a scanning range corresponding to the [portion specified by the arithmetic analysis unit] *specified portion*.

5. The fundus observation apparatus according to claim 4, wherein the [arithmetic analysis unit is arranged to determine] *first program further causes the processor to execute determining* the second tomographic image and [obtain] *obtaining* a second determination result, and the [information display unit is arranged to] display *displays* the first and second tomographic images and the first and second determination results [that are obtained by the arithmetic analysis unit].

6. The fundus observation apparatus according to claim 4, wherein the [control unit is arranged to set] *second program further causes the controller to execute setting* the scanning range for obtaining the second tomographic image to be a scanning range that is narrower than the scanning range for obtaining the first tomographic image and includes the whole specified portion.

7. The fundus observation apparatus according to claim 4, wherein the [control unit is arranged to set] *second program further causes the controller to execute setting* a scanning pattern of the measurement light according to the specified portion.

8. The fundus observation apparatus according to claim 4, wherein the [arithmetic analysis unit is arranged to specify] *first program further causes the processor to execute specifying* a region corresponding to [a] *the* macula portion in the first tomographic image through the image processing, and perform determination appropriate to the specified region.

9. The fundus observation apparatus according to claim 4, wherein the [arithmetic analysis unit is arranged to specify] *first program further causes the processor to execute specifying* a region corresponding to [a] *the* papilla portion in the first tomographic image through the image processing, and perform determination appropriate to the specified region.

10. The fundus observation apparatus according to claim 4, wherein the [control unit is arranged to set] *second program further causes the controller to execute setting* the scanning range for obtaining the second tomographic image by obtaining a scanning position of the optical scanner corresponding to the specified portion based on a relation between the first tomographic image and a scanning position of the optical scanner.

11. The fundus observation apparatus according to claim 4, wherein the [control unit is arranged to perform] *second program further causes the controller to execute performing* matching between a tomographic image corresponding to the specified portion in the first tomographic image and [a] tomographic [image] *images* obtained when obtaining the second tomographic image through the image processing, and [correct] *correcting* a scanning position of the optical scanner so as to obtain a *matching* topographic image *among the tomographic images obtained when obtaining the second tomographic image* at a substantially matching position.

[12. The fundus observation apparatus according to claim 1, further comprising:

a front fundus image pickup device that is arranged to obtain a front image of the fundus, wherein the arithmetic analysis unit is arranged to detect brightness information on the front image obtained by the front fundus image pickup device through the image processing, and determine the front image by determining the detected brightness information by a given determination criterion.]

13. The fundus observation apparatus according to claim [12] *1*, wherein the [arithmetic analysis unit is arranged to specify] *first program further causes the processor to execute specifying* one of a targeted image pickup portion and the abnormal portion based on determination results of the tomographic image and the front image that are obtained [by the arithmetic analysis unit] through the image processing, and the [control unit is arranged to adjust] *second program further causes the controller to execute adjusting* the image pickup position so as to obtain the tomographic image including the specified portion.

*14. The fundus observation apparatus according to claim 1, wherein the plurality of photographing modes comprises a mode for photographing both a macula portion and a papilla portion.*

*15. The fundus observation apparatus according to claim 1, wherein the second program further causes the controller to execute controlling a scanning position of the optical scanner depending on the photographing mode in controlling the driving of the optical coherence tomography device depending on the photographing mode.*

*16. The fundus observation apparatus according to claim 1, wherein the displayed assisting information includes the presence or absence of an abnormality in the image pickup positions related to the photographing modes.*

* * * * *